United States Patent
Haq et al.

(12) 
(10) Patent No.: US 6,360,883 B1
(45) Date of Patent: Mar. 26, 2002

(54) PACKAGING FOR ARTIFICIAL LENS

(75) Inventors: Anwar Haq, Corona; Scott M. Hampton, Claremont, both of CA (US)

(73) Assignee: Opthalmic Innovations, Inc., Claremont, CA (US)

( * ) Notice: Subject to any disclaimer, the term of this patent is extended or adjusted under 35 U.S.C. 154(b) by 0 days.

(21) Appl. No.: 09/264,800

(22) Filed: Mar. 9, 1999

(51) Int. Cl.[7] ............................................. B65D 81/24
(52) U.S. Cl. ........................................ 206/205; 206/5.1
(58) Field of Search ........................... 53/449; 206/205, 206/210, 5.1, 438, 5

(56) References Cited

U.S. PATENT DOCUMENTS

| | | | |
|---|---|---|---|
| 3,150,406 A | * | 9/1964 | Obitts .................... 206/5.1 |
| 3,233,727 A | | 2/1966 | Wilson |
| 3,309,893 A | | 3/1967 | Heffler et al. |
| 3,314,533 A | | 4/1967 | Kopfle |
| 4,200,187 A | * | 4/1980 | Thomas .................. 206/5.1 |
| 4,311,792 A | | 1/1982 | Avery |
| 4,691,725 A | * | 9/1987 | Parisi .................... 206/5.1 |
| 5,000,209 A | | 3/1991 | Mann |
| 5,114,686 A | * | 5/1992 | Gillespie ................ 206/5.1 |
| 5,373,980 A | | 12/1994 | Rowell et al. |
| 5,402,810 A | | 4/1995 | Donley |
| 5,467,868 A | | 11/1995 | Abrams et al. |
| 5,538,301 A | * | 7/1996 | Yavitz et al. ............ 206/5.1 |
| 5,573,108 A | | 11/1996 | Hamilton et al. |
| 6,244,430 B1 | * | 6/2001 | Travis .................... 206/5.1 |

FOREIGN PATENT DOCUMENTS

| | | |
|---|---|---|
| DE | WO9409399 | 4/1994 |
| JP | 0073947 | 4/1986 |

* cited by examiner

*Primary Examiner*—Jim Foster
(74) *Attorney, Agent, or Firm*—Sheldon & Mak; Denton L. Anderson

(57) ABSTRACT

A package suitable for carrying an artificial lens which includes a container and a removable insert disposed within the container. The removable insert defines an enclosed insert chamber sufficiently large to hold the artificial lens. The removable insert has insert walls which are sufficiently thin to allow the manipulation of an artificial lens disposed within the insert chamber by applying mechanical force to the exterior of the insert walls. Typically the removable insert is attached to a container cap or other container closure structure having a downwardly directed projection member. In this embodiment, the simple removal of the container cap from the container coincidentally removes the removable insert from the container.

21 Claims, 3 Drawing Sheets

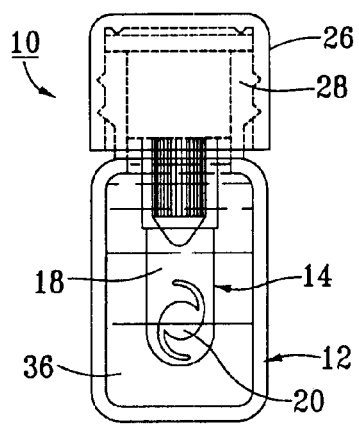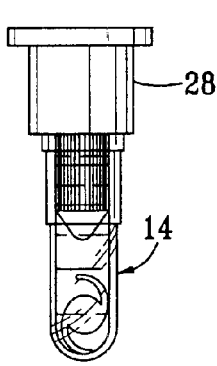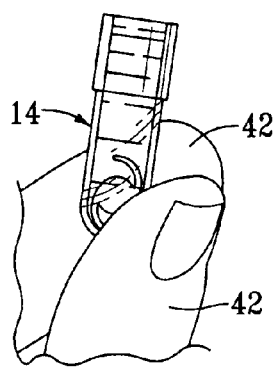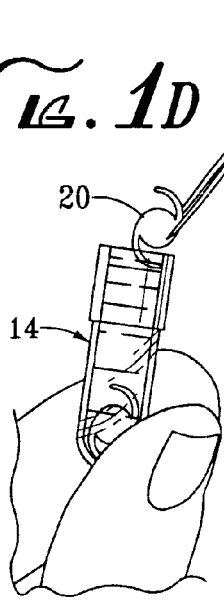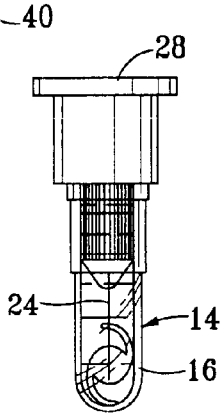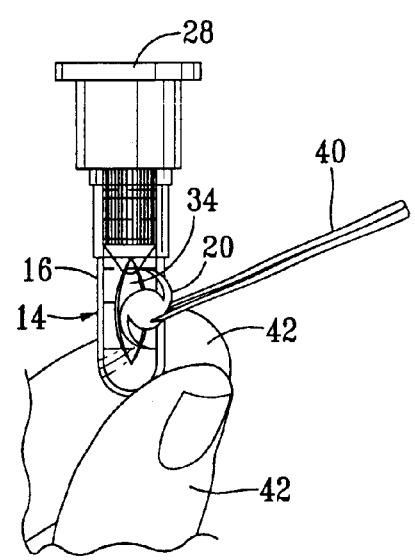

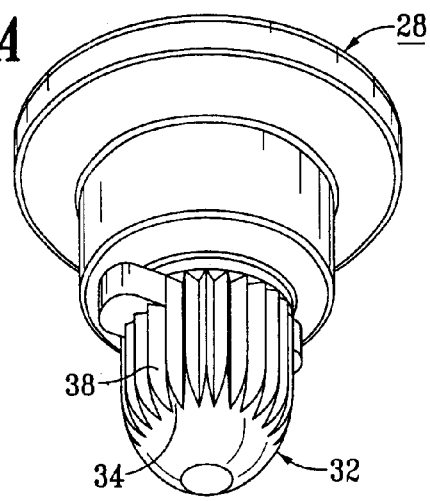
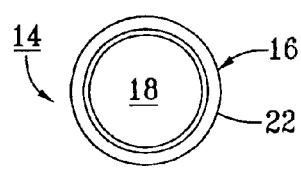
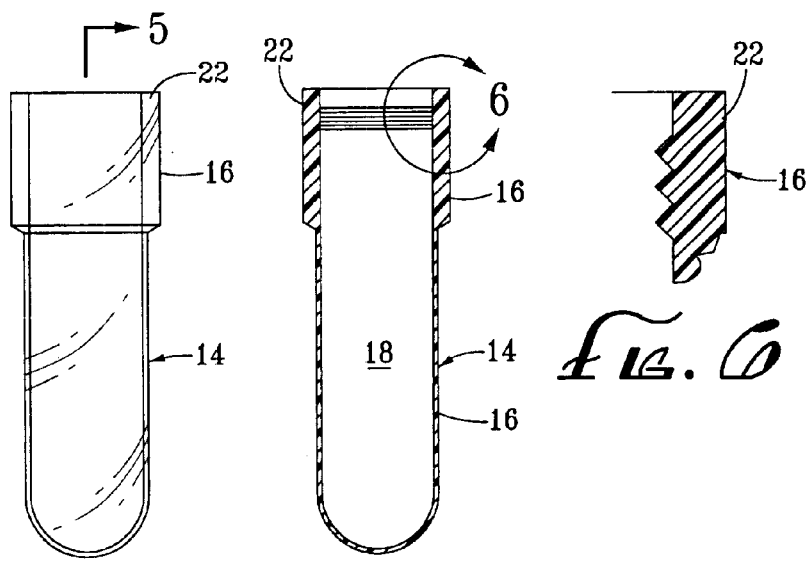

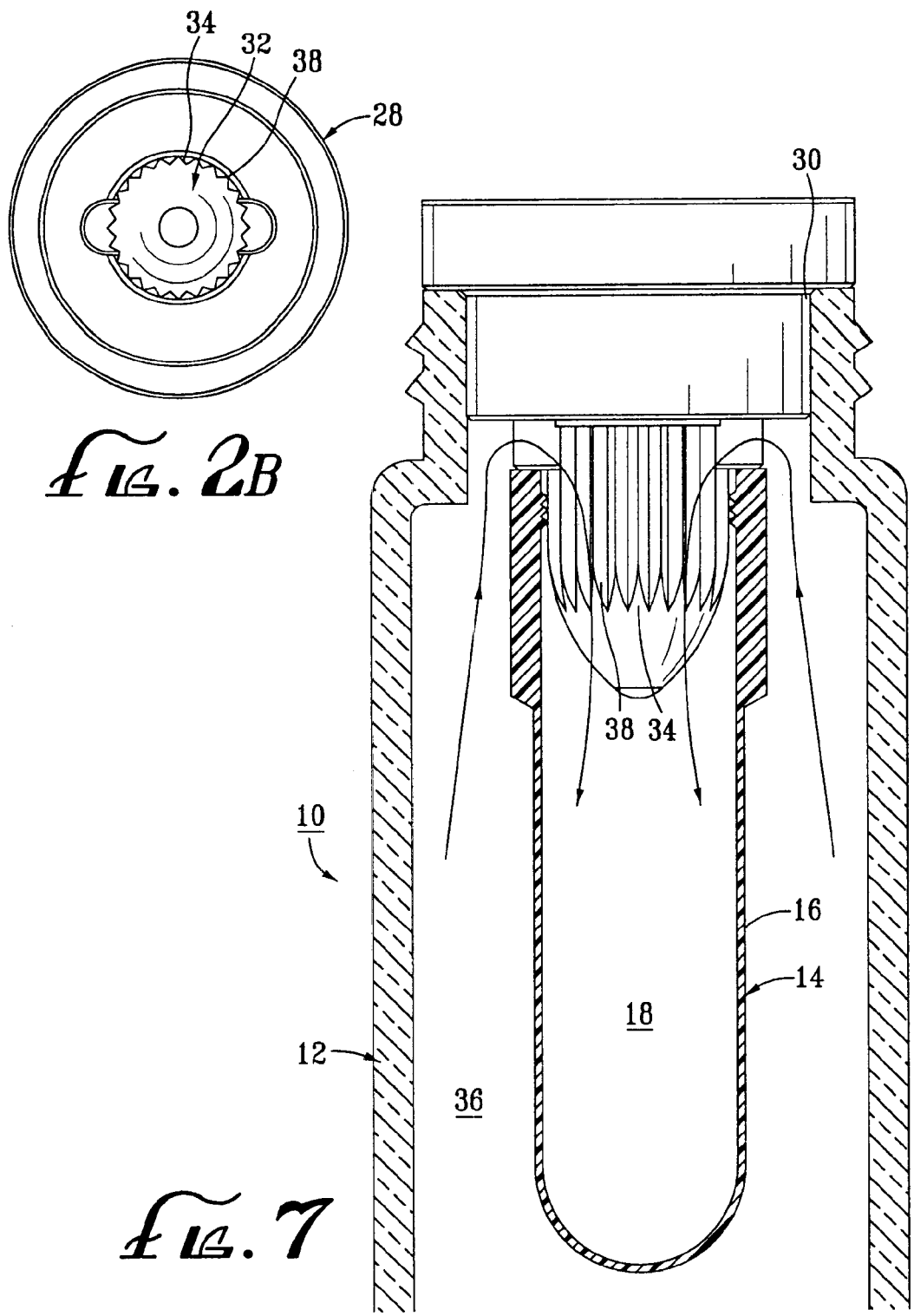

PACKAGING FOR ARTIFICIAL LENS

FIELD OF THE INVENTION

This invention relates generally to artificial lenses, and more specifically, to packaging used in the distribution of artificial lenses.

BACKGROUND

The use of artificial lenses has become a very important method for remedying a wide variety of ophthalmic problems. Artificial lenses include lenses disposed on the exterior of the patient's eyes (e.g., contact lenses) and lenses disposed within the eye itself ("intraoccular lenses").

Artificial lenses must generally be packaged in saline solution to prevent the lenses from drying out. A typical package for artificial lenses is a sealed glass vial wherein the artificial lens is submerged within a suitable quantity of saline solution.

A continuous problem with respect to such packaging is the difficulty of extracting the lens from the vial. If the user attempts to extract the lens by pouring the saline from the vial, the lens tends to remain within the vial, adhered to the interior wall of the vial. If the user attempts to extract the lens using an extraction instrument, the lens moves freely within the saline solution, making it difficult to grasp the lens in a way which will not damage the lens. This is especially true because most lenses are transparent and difficult to see within the saline solution.

The problem of extracting artificial lenses from saline-containing packaging is most acute in the case of intraoccular lenses. Such lenses are generally much smaller than contact lenses, having a nominal diameter generally less than about 8 millimeters. Moreover, intraoccular lenses are frequently made from highly hydrated materials which are easily damaged by mechanical instruments.

Accordingly, there is a need for improved artificial lens packaging which will avoid the problems with prior art in an efficient and inexpensive manner.

SUMMARY

The invention satisfies this need. The invention is a combination suitable for packaging an artificial lens comprising (a) a container encompassing a volume between about 1 cubic centimeter and about 7 cubic centimeters, and (b) a removable insert disposed within the container, the insert comprising insert walls which define an enclosed insert chamber sufficiently large to hold an artificial lens, the insert walls being sufficiently thin to allow manipulation of an artificial lens disposed within the insert chamber by applying mechanical force to the exterior of the insert walls.

In a typical embodiment, the container is a glass vial having enclosure means and the removable insert is an elastomeric nipple attached to the enclosure means.

The invention greatly simplifies the procedure by which artificial lenses can be removed from the combination of the invention. In a typical embodiment, the user need merely to remove the enclosure means carrying the elastomeric nipple, grasp the artificial lens through the walls of the nipple, and extracting the artificial lens from the nipple, using a forceps or other suitable tool. The invention is especially useful in the packaging of intraoccular lenses made of soft acrylic and other hydrophilic materials.

DESCRIPTION OF THE DRAWINGS

These features, aspects and advantages of the present invention will become better understood with regard to the following description, appended claims and accompanying figures where:

FIG. 1A is a side view of a combination having features of the invention;

FIG. 1B is a side view of an insert and cap portion of the combination illustrated in FIG. 1A;

FIG. 1C illustrates a insert portion of the combination illustrated in FIGS. 1A and 1B, held in the fingers of a user;

FIG. 1D illustrates an artificial lens being removed from the insert illustrated in FIG. 1C;

FIG. 2A is a perspective view of a seal useful in the combination illustrated in FIG. 1A;

FIG. 2B is a bottom view of the seal illustrated in FIG. 2A;

FIG. 3 is a side view of a insert useful in the combination illustrated in FIG. 1A;

FIG. 4 is a top view of the insert illustrated in FIG. 3;

FIG. 5 is a cross-sectional side view of the insert illustrated in FIG. 3, taken along line 5—5;

FIG. 6 is a detail view of the upper-most perimeter of the insert illustrated in FIG. 5;

FIG. 7 is a cross-sectional detail view of a combination having features of the invention;

FIG. 8 is a side view of an alternative insert and cap useful in the invention; and FIG. 9 is another side view of the insert and cap illustrated in FIG. 8, the illustration in FIG. 9 showing the removal of an artificial lens through a slit in the side of the insert.

DETAILED DESCRIPTION

The following discussion describes in detail one embodiment of the invention and several variations of that embodiment. This discussion should not be construed, however, as limiting the invention to those particular embodiments. Practitioners skilled in the art will recognize numerous other embodiments as well.

The invention is a combination 10 comprising a container 12 and a removable insert 14 disposed within the container 12.

The container 12 encompasses a volume between about 1 cc and about 7 cc. The container 12 is typically a small glass vial, although the container 12 can be made from any other suitable material.

The insert 14 has insert walls 16 which define an enclosed insert chamber 18 sufficiently large to hold an artificial lens 20. Typically the volume of the insert chamber 18 is between about 0.2 cc and about 4 cc.

The insert walls 16 are sufficiently thin to allow the manipulation of an artificial lens 20 disposed within the insert chamber 18 by applying mechanical force to the exterior of the insert walls 16. Typically this means that the insert walls 16 are sufficiently thin to allow the user to tactilely sense an artificial lens 20 disposed within the insert chamber 18. The thickness of the insert walls 16 will depend upon the material used in their construction. Where the insert 14 is made from an elastomeric material such a silicone, latex or nitrile, the thickness of the insert walls 16 is typically between about 0.01 mm and about 1.5 mm, preferably between about 0.02 mm. and about 0.06 mm. Silicone has been found to be a most suitable material of construction for the insert 14.

In a preferred embodiment, the upper end 22 of the removable insert 14 is reenforced. For example, in the embodiment illustrated in the drawings, the upper end 22 of the removable insert 14 has thickened walls 16 which can be between about 1 mm and about 3 mm in thickness.

Preferably, the insert walls 16 are sufficiently transparent to allow an artificial lens 20 to be seen through the insert walls 16.

In a typical embodiment, the insert chamber 18 is defined by generally cylindrical insert walls 16 having a diameter between about 0.8 cm and about 1 cm and having a length between about 2.5 cm and about 3 cm.

The removable insert 14 has opening means for the insertion and removal of an artificial lens 20 to and from the insert chamber 18. In the embodiments illustrated in the FIGS. 8 and 9, such opening means comprises a longitudinal slit 24 disposed within the side walls 16 of the insert chamber 18. In such an embodiment, the longitudinal slit 24 can be opened, as illustrated in FIG. 9, by simply squeezing the exterior of the insert walls.

Typically, the container 12 also includes removable closure means for sealing the container 12. In the embodiment illustrated in the drawings, such closure means includes a removable container cap 26 and a removable elastomeric seal 28. In this embodiment, the elastomeric seal 28 is disposed within the container opening 30 and is firmly retained by the container cap 26. By this method, the container 12 can be sealed to prevent the leakage of saline from the container 12.

In the embodiment illustrated in the drawings, the seal 28 has a downwardly directed projection member 32 which is disposed within the container 12. The removable insert 14 is attached to this projection member 32. The removable insert 14 may be removably attached to the projection member 32 to allow the removal of the artificial lens 20 from the upper end 22 of the removable insert 14. Alternatively, the removable insert 14 can be permanently attached to the projection member 32 so long as other appropriate opening means are provided.

It is important in the invention that passageways 34 be provided in the combination to allow fluid communication between the insert chamber 18 and the external volume 36 encompassed by the container which is disposed external of the insert 14. Such passageways 34 allow the "bathing" of the artificial lens within the removable insert by the full volume of saline disposed within the container. In the embodiment illustrated in the drawings, such passageways 34 are provided at the uppermost end 22 of the insert walls 16. In this embodiment, the uppermost end 22 of the insert walls 16 is not completely sealed to the downwardly directed projection member 32, so the fluids within the insert chamber 18 can freely communicate with fluids external of the insert 14. Such incomplete sealing can be accomplished by providing the downwardly directed projection member 32 with bumps 38 which prevent the upper-most end 22 of the removable insert 14 to completely seal to the projection member 32. In the embodiment illustrated in the drawings, such bumps 38 are vertically disposed, parallel ribs, each between about 0.1 mm and about 0.2 mm in height.

The invention is advantageous for packaging intraoccular lenses, such as those made from silicone and acrylics. The invention is inexpensive to manufacture, easy to sterilize and easy to load. The invention is especially advantageous for packaging intraoccular lenses made from highly hydrated material such as hydrophilic acrylics.

In operation, the packager of artificial lenses 20 sterilizes each of the appropriate components of the invention 10. Thereafter, the removable insert 14 is "loaded" with an artificial lens 20 by insertion of the artificial lens 20 into the insert chamber 18 using the opening means. The container is then filled with an appropriate saline solution. The removable insert 14 is attached to the elastomeric seal 28 and the seal 28 is firmly retained across the opening 30 of the container 12 by the container cap 26.

When a medical practitioner wishes to gain access to the artificial lens 20, the practitioner removes the container cap 26 and withdraws the elastomeric seal 28 from the container 12. In withdrawing the elastomeric seal 28 from the container 12, the removable insert 14 is withdrawn from the container 12 as well.

Once the removable insert 14 is removed from the container 12, the practitioner grasps the artificial lens 20 by gently applying pressure to the external sides of the insert walls 16. The practitioner is aided in this regard by being able to see the lens 20 within the insert chamber 18, because the insert walls 16 are sufficiently transparent. While grasping the lens 20 through the walls 16 of the removable insert 14, the practitioner gains access to the insert chamber 18 using the opening means. Then, the practitioner uses a forceps or other insertion tool 40 to directly grasp the lens 20 and remove the lens 20 from the insert chamber 18. During this step, the practitioner does not have to "fish" for the lens 20 within the insert chamber 18 because the practitioner is able to firmly retain the lens 20 between the practitioner's fingertips 42 as he applies pressure to the external sides 16 of the removable insert 14.

Having thus described the invention, it should be apparent that numerous structural modifications and adaptations may be resorted to without departing from the scope and fair meaning of the instant invention as set forth hereinabove and as described hereinbelow by the claims. In this regard, any element in a claim that does not explicitly state "means" for performing a specified function, or "step" for performing a specified function should not be interpreted as a "means" or a "step" clause as specified in 35 U.S.C. §112.

What is claimed is:

1. A combination comprising:
   (a) a container encompassing a volume between about 1 cubic centimeter and about 7 cubic centimeters;
   (b) a removable insert disposed within the container, the insert comprising insert walls which define an enclosed insert chamber sufficiently large to hold an artificial lens, the insert walls being sufficiently thin to allow manipulation of an artificial lens disposed within the insert chamber by applying mechanical force to the exterior of the insert walls; and
   (c) an intraocular lens disposed within the removable insert.

2. The combination of claim 1 wherein the volume of the insert chamber is between about 0.2 cubic centimeters and about 4 cubic centimeters.

3. The combination of claim 1 wherein the insert walls are sufficiently thin to allow the user to tactily sense the intraocular lens disposed within the insert chamber.

4. The combination of claim 1 wherein the insert walls are made from a material chosen from the group of materials which consists of silicone, latex and nitrile.

5. The combination of claim 1 wherein the insert walls are made from silicone.

6. The combination of claim 1 wherein the thickness of the insert walls is between about 0.01 mm and about 1.5 mm.

7. The combination of claim 1 wherein the thickness of the insert walls is between about 0.02 mm and about 0.06 mm.

8. The combination of claim 1 wherein the insert walls are substantially transparent.

9. The combination of claim 1 wherein the removable insert has opening means for insertion and removal of the intraocular lens to and from the insert chamber.

10. The combination of claim 1 wherein the removable insert has a slit for insertion and removal of the intraocular lens to and from the insert chamber.

11. The combination of claim 1 wherein the container includes removable enclosure means and wherein the insert is attached to the closure means, so that the insert is removed from the container by the removal of the closure means.

12. The combination of claim 11 wherein the closure means comprises a container cap which is reversibly attachable to the container.

13. The combination of claim 12 wherein the closure means further comprises an elastomeric seal.

14. The combination of claim 13 wherein the elastomeric seal has a downwardly directed projection member.

15. The combination of claim 1 further comprising passageways to allow fluid communication between the insert chamber and the volume encompassed by the container which is disposed external of the insert chamber.

16. The combination of claim 11 wherein the insert walls define an upper-most perimeter and wherein the insert walls are attached to, but not completely sealed to, the enclosure means, such that fluids within the insert chamber can freely communicate with fluids external of the insert chamber.

17. The combination of claim 16 wherein the upper-most perimeter of the insert walls is attached to a downwardly directed projection member attached to the enclosure means and wherein the projection member contains bumps to allow fluid communication between liquid within the insert chamber and liquid external of the insert chamber.

18. The combination of claim 17 wherein the bumps are vertically disposed ribs.

19. A method for packaging an intraocular lens comprising:

(a) selecting a combination comprising:
  (i) a container encompassing a volume between about 1 cubic centimeter and about 7 cubic centimeters; and
  (ii) a removable insert disposed within the container, the insert comprising insert walls which define an enclosed insert chamber sufficiently large to hold an intraocular lens, the insert walls being sufficiently thin to allow manipulation of an intraocular lens disposed within the insert chamber by applying mechanical force to the exterior of the insert walls;

(b) placing the intraocular lens within the insert chamber;

(c) adding an aqueous fluid to the container and to the insert chamber; and (d) sealing the container to prevent the leakage of the aqueous fluids from the container.

20. A combination suitable for packaging an artificial lens comprising:

(a) a container encompassing a volume between about 1 cubic centimeter and about 7 cubic centimeters; and (b) a removable insert disposed within the container, the insert comprising insert walls which define an enclosed insert chamber sufficiently large to hold an artificial lens, the insert walls being sufficiently thin to allow manipulation of an artificial lens disposed within the insert chamber by applying mechanical force to the exterior of the insert walls;

wherein the removable insert has opening means for insertion and removal of an artificial lens to and from the insert chamber.

21. The combination of claim 20 wherein the opening means is a slit.

* * * * *